United States Patent [19]

Hammond et al.

[11] 4,079,082
[45] Mar. 14, 1978

[54] LASING DYES DERIVED FROM TER-AND QUATERPHENYL

[75] Inventors: Peter R. Hammond, Livermore; Theodore G. Pavlopoulos, San Diego, both of Calif.

[73] Assignee: The United States of America as represented by the Secretary of the Navy, Washington, D.C.

[21] Appl. No.: 572,590

[22] Filed: Apr. 28, 1975

[51] Int. Cl.$^2$ .................. C07C 87/50; C07C 39/12
[52] U.S. Cl. ................................ 260/576; 260/580; 260/619 B
[58] Field of Search .............................. 260/580, 576

[56] References Cited

U.S. PATENT DOCUMENTS 3,342,865  9/1967  Oberster .................... 260/576

OTHER PUBLICATIONS

Pavlopoulos et al., "Journal of the American Chemical Society", 96:21, pp. 6568 to 6579, (1974).
Colonge et al., "Bull. Soc. Chim. Fr.", vol. 11, pp. 4370–4374, (1967).
Mason et al., "J. Chem. Soc.", pp. 1379–1385, (1940).
Amos et al., "Aust. J. Chem.", vol. 22(7), pp. 1555–1556, (1969).
Price et al., "J. Am. Chem. Soc.", vol. 66, pp. 632–634, (1944).
Scheinbaum, "J. Chem. Soc. PT D", vol. 21, p. 1235, (1969).

*Primary Examiner*—Daniel E. Wyman
*Assistant Examiner*—John J. Doll
*Attorney, Agent, or Firm*—R. S. Sciascia; Roy Miller

[57] ABSTRACT

Methods for preparing

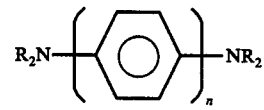

wherein n is 3 or 4 and R is H, $CH_3$ or $C_2H_5$. The methods involve forming

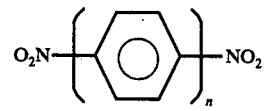

by reacting p-terphenyl or quaterphenyl with acetic acid and fuming nitric acid, forming

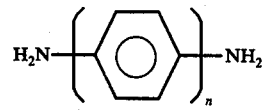

by refluxing the dinitro derivative with stannous chloride, hydorchloric acid and acetic acid and forming the dialkylamino derivative by refluxing the diamino derivatives with a suitable trialkyl phosphate. Also,

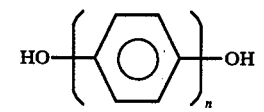

derivatives may be prepared by refluxing the diamino derivatives with sodium nitrite and hydrochloric acid to form

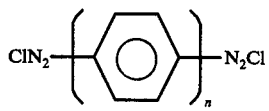

and reacting this intermediate with a mixture of acetic acid and either water or alcohol. The compounds are useful as lasing dyes.

1 Claim, No Drawings

LASING DYES DERIVED FROM TER-AND QUATERPHENYL

BACKGROUND OF THE INVENTION

1. Field of the Invention

This invention relates to the use of dyes in lasers and to the preparation of such dyes. More particularly, this invention relates to the use of dyes to lase in the violet to blue-green portion of the spectrum and to the preparation of such dyes.

2. Description of the Prior Art

Experimental work directed toward determiing the practicality of using dye lasers in underwater communication and the like is presently being carried out. To be useful in a laser that is to be applied underwater, a dye must include the following properties. It must lase in the transmission region of sea water and it should be relatively stable. That is, it is not desirable to have to change the dye in a dye laser frequently in order to produce good results.

Many dyes are, of course, known to lase when placed, in solution, in a laser and pumped. However, to the best of the inventor's knowledge the hereinafter disclosed dyes have not been disclosed as being useful as lasing dyes. Some of the hereinafter disclosed dyes have been previously prepared. Others, to the best of the inventor's knowledge, have not. In all cases, new and improved methods of preparation are believed to be disclosed.

SUMMARY OF THE INVENTION

Certain derivatives of terphenyl and quaterphenyl have recently been discovered to have the above-mentioned desirable lasing dye qualities. The derivatives have the structures:

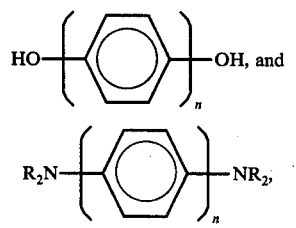

where R is H, $CH_3$ or $C_2H_5$ and where $n$ is 3 or 4. These terphenyl and quaterphenyl derivatives can be tuned to lase in the blue-green to violet regions and are stable for long periods of time, i.e., do not decompose, even when they are frequently pumped.

DESCRIPTION OF THE PREFERRED EMBODIMENTS

The starting compounds in preparing the derivatives of this invention are terphenyl and quaterphenyl. Both these compounds have been known since the late 1930's. To prepare 4,4'-diamino-p-terphenyl, the first step is to prepare 4,4'-dinitro-p-terphenyl. A description of this step appears in Example 1.

EXAMPLE 1

4,4'-Dinitro-p-Terphenyl

To a stirred refluxing solution of p-terphenyl (10.0g) in glacial acetic acid (500ml), fuming nitric acid (75ml, d 1.5) in acetic acid (50 ml) was added over a period of fifteen minutes. After the addition was complete, the reflux was continued for another hour and fifteen minutes. On cooling, 4.4g (32% yield) of pale yellow 4,4'-dinitro-p-terphenyl crystals deposited. These crystals were purified by recrystallizing from pyridine.

Anal: Found, C 67.58; H 3.75; N 8.76 - Required, C 67.5; H 3.75; N 8.74%. The melting point was determined to be 274°–275° C.

The NMR spectrum in hot dimethyl sulfoxide appeared as an aromatic singlet superimposed on an $A_2B_2$ quartet so as to obscure the high field peak of the quartet.

The next, and final, step in preparing 4,4'-diamino-p-terphenyl is described in Example 2.

EXAMPLE 2

4,4'-Diamino-p-Terphenyl

The dinitro derivative from Example 1 (10g) was dissolved in glacial acetic acid (1.51) and refluxed. To the refluxing solution, stannous chloride dihydrate (50g) in 50ml of concentrated hydrochloric acid was slowly added over fifteen minutes. After the addition was complete, the reflux was continued for another fifteen minutes. Upon cooling, a dark grey precipitate appeared. This was filtered off, washed with water, boiled in 100ml of 20% aqueous sodium hydroxide and washed with water again. During the washing process, the precipitate turned from grey to orange. To further purify the material, it was refluxed in pyridine with decolorizing charcoal, filtered through Whatman No. 2 paper, and was crystallized from 40% aqueous pyridine. Analysis proved the material to be 4,4'-diamino-p-terphenyl.

Anal: Found, C 83.02; H 6.18; N 10.64 — Required, C 83.2; H 6.14, N 10.75. The final purified product was light brown in color. Six grams (74% yield) were obtained.

The NMR spectrum in dimethyl sulfoxide included a singlet at 7.69 downfield of an $A_2B_2$ quartet at 7.61, 7.48, 6.88 and 6.77 with a ratio of the integrated intensities being 1:2.

N,N,N',N'-Tetraethyl-4,4'-diamino-p-terphenyl may be prepared according to Example 3.

EXAMPLE 3

N,N,N',N'-Tetraethyl-4,4'-diamino-p-terphenyl 4,4'-Diamino-p-terphenyl (4.0g) in triethyl phosphate (40ml) was refluxed in an oil bath for five hours. The mixture was then suspended in 200ml of 4N hydrochloric acid. Filtered, and made alkaline with 10% sodium hydroxide. The resulting precipitate was washed with water and recrystallized from dioxane-water (4:1) to give light buff crystals (3.1g, 55% yield, m.p. 190–191. S°C). Analysis proved the crystals to be tetraethylamino derivative.

Anal: Found, C 83.71; H 8.46; N 7.41 — Required, C 83.8; H 8.59; N 7.52.

The NMR spectrum in deuterochloroform showed the ethyl triplet and quartet centered at 1.20 and 3.42 respectively. The aromatic protons which appeared as a singlet at 7.62 were superimposed on an $A_2B_2$ quartet at 7.49, 6.87 and 6.72 so as to obscure the low field peak of the quartet. Integrated intensities were in accord with the proposed structure.

The tetramethyl derivative may be prepared in the manner of Example 3 by substituting trimethyl phosphate for triethyl phosphate.

To form 4,4'-diamino-quaterphenyl, one first forms 4,4'-dinitro-quaterphenyl and then reacts it. 4,4'-Dinitro-quaterphenyl may be formed by following the procedure of Example 4.

EXAMPLE 4

4,4'-Dinitro-Quaterphenyl

Quaterphenyl (2.00g) was stirred in a refluxing glacial acetic acid (225ml), nitrobenzene (225ml) mixture until dissolved. Fuming nitric acid (d 1.5, 15ml) in acetic acid (60ml) was added over ten minutes. The mixture was further refluxed for fifty minutes. Upon cooling the flask in ice, yellow crystals appeared. They were recrystallized from chlorobenzene (0.85g, 33%). Upon heating, the material became mobile at 307° C with previous softening but did not clear even at 340° C when slow charring ocurred.

Anal: Found, C 72.68, H 3.98; N 6.98 — Required, C 72.8; H 4.03; N 7.06%.

The time averaged NMR spectrum in hot dimethyl sulfoxide appeared as a singlet superimposed on an $A_2B_2$ quartet with the singlet covering the high field peak of the quartet.

4,4'-Diamino-quaterphenyl can be prepared from the 4,4'-dinitro derivative by following the procedure of Example 5.

EXAMPLE 5

4,4'-Diamino-Quaterphenyl 4,4'-Dinitro-quaterphenyl from Example 4 (2.70g) and stannous chloride (12.0g) were suspended in stirred, refluxing acetic acid (200ml) and dry hydrogen chloride was slowly bubbled through the mixture for five hours. The precipitate was boiled in 20% aqueous sodium hydroxide, filtered, washed and crystallized from 10% aqueous pyridine. The diamine was obtained as a light buff colored solid. A 60% yield (1.4g) was obtained. It had a melting point of 304° C with charring.

Anal: Found, N 8.00 — Required N 8.32%.

The NMR spectrum in dimethyl sulfoxide included an aromatic singlet 7.52 to low field of an $A_2B_2$ quartet 7.37, 7.22, 6.59 and 6.44 with integrated intensities in the ratio 1:1. N,N,N', N'-Tetraethyl-4,4'-diamino-quaterphenyl may be prepared from the diamino derivative of Example 5 by following the procedure outlined in Example 6.

EXAMPLE 6

N,N,N',N'-Tetraethyl-4,4'-Diamino-Quaterphenyl

The diamino derivative (2.5g) in triethyl phosphate (25ml) was refluxed in an oil bath for six hours. The solution was then mixed with 100ml concentrated hydrochloric acid, filtered and made alkaline with aqueous sodium hydroxide. The precipitate was crystallized from pyridine-ethanol to give 2.1g (63% yield) of light buff crystals, m.p. 261.5–262.5.

Anal: Found, C 85.67; H 7.99; N 6.19 — Required, C 85.7; H 8.03; N 6.24%.

The NMR spectrum in deuterochloroform showed the ethyl triplet and quartet centered at 1.22 and 3.46. The aromatic signals appeared as a singlet 7.71 superimposed on a $A_2B_2$ quartet 7.53, 6.89, 6.75 so as to obscure the low peak field. Integrated intensities were in accord with the proposed structure.

N,N,N', N'-Tetramethyl-4,4'-diamino-quaterphenyl may be prepared by substituting trimethyl phosphate for the triethyl phosphate utilized in Example 6. If one takes either the 4,4'-diamino derivative of terphenyl (from Example 2) or the corresponding derivative of quaterphenyl (from Example 5) and reacts it with NaNO$_2$ (sodium nitrite) and HCl (hydrochloric acid) the following reaction occurs:

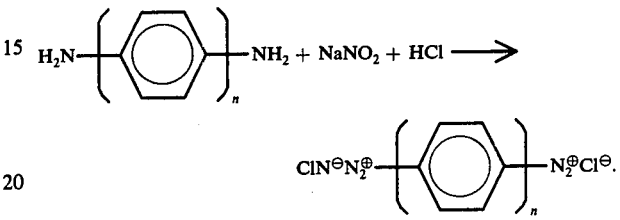

When one heats the chloride salt in either H$_2$O and alcohol or H$_2$O and acetic acid, the following reaction occurs:

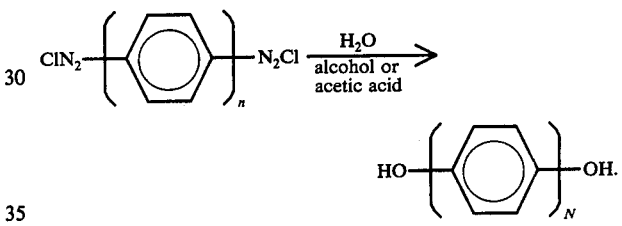

In this way, 4,4'-dihydroxy-p-terphenyl or 4,4'-dihydroxy-quaterphenyl may be formed.

EXAMPLE 7

To determine whether or not the foregoing dyes lased, solutions of them were made up, placed in an Avco-Everett, C-400, nitrogen laser-dye laser combination and pumped. All of the dyes lased in the transmission region of sea water. For the diamino derivatives (both terphenyl and quaterphenyl) the solution tested was a $2 \times 10^{-3}$ M solution of the dye in dimethyl sulfoxide. For the tetramethyl diamino derivative of terphenyl, a saturated solution of the dye in methyl cellusolve was used. For the tetraethyl diamino derivative of quaterphenyl, a saturated solution of the dye in dichloromethane was used. For the hydroxides, solutions similar to those used for the diamino derivatives are suitable.

What is claimed is:

1. A compound having the structure:

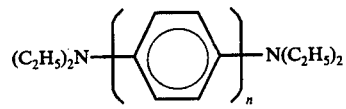

wherein n is 3 or 4.